(12) United States Patent
van den Engh

(10) Patent No.: US 7,345,758 B2
(45) Date of Patent: Mar. 18, 2008

(54) APPARATUS FOR ANALYZING AND SORTING BIOLOGICAL PARTICLES

(75) Inventor: Ger van den Engh, Seattle, WA (US)

(73) Assignee: Cytopeia, Seattle, WA (US)

( * ) Notice: Subject to any disclaimer, the term of this patent is extended or adjusted under 35 U.S.C. 154(b) by 513 days.

(21) Appl. No.: 09/860,621

(22) Filed: May 17, 2001

(65) Prior Publication Data

US 2002/0171827 A1    Nov. 21, 2002

(51) Int. Cl.
    *G01J 3/30* (2006.01)
(52) U.S. Cl. .......................... 356/317; 356/72
(58) Field of Classification Search ............... 356/72, 356/73, 317, 318; 250/458.1–461.2
See application file for complete search history.

(56) References Cited

U.S. PATENT DOCUMENTS

| | | | |
|---|---|---|---|
| 3,813,172 A | 5/1974 | Walker et al. .............. 356/225 |
| 4,801,810 A | 1/1989 | Koso ........................... 250/572 |
| 5,247,340 A * | 9/1993 | Ogino .......................... 356/73 |
| 5,602,039 A | 2/1997 | Van den Engh | |
| 5,602,349 A | 2/1997 | Van den Engh | |
| 5,608,526 A | 3/1997 | Piwonka-Corle et al. ... 356/369 |
| 5,693,484 A * | 12/1997 | Nakamoto et al. ............ 356/73 |
| 5,819,948 A | 10/1998 | Van den Engh | |
| 6,003,678 A | 12/1999 | Van den Engh | |
| 6,067,157 A | 5/2000 | Altendorf ................. 356/337 |
| 6,133,044 A | 10/2000 | Van den Engh | |
| 6,353,657 B1 | 3/2002 | Bayrock et al. .......... 378/98.3 |

OTHER PUBLICATIONS

Shapiro, *Practical Flow Cytometry*, Wiley-Liss, Inc., Chapter 1, pp. 1-31, Chapter 4, pp. 75-177, Chapter 6, pp. 217-228 (1995).
Asbury et al., "Polarization of Scatter and Fluorescence Signals in Flow Cytometry," *Cytometry*, 40:88-101 (2000).
International Society for Analytical Cytology: Letter of Acceptance and Registration Confirmation for Ger van den Engh.

* cited by examiner

*Primary Examiner*—James Phan
(74) *Attorney, Agent, or Firm*—McDermott Will & Emery

(57) ABSTRACT

The invention provides an apparatus including (a) a frame having a boundary plane; (b) a flow chamber supported by the frame, the flow chamber placed a distance from the boundary plane; (c) a radiation source, the radiation source directed away from the flow chamber and away from the exterior side of the boundary plane, and (d) a first reflective surface placed to direct a radiation beam in a path crossing the boundary plane to the flow chamber; (e) one or more reflective surfaces placed to direct a radiation beam from the radiation source to the first reflective surface, the path from the radiation source to the flow chamber being at least 1.5 times the distance from the flow chamber to the boundary plane.

35 Claims, 6 Drawing Sheets

APPARATUS FOR ANALYZING AND SORTING BIOLOGICAL PARTICLES

BACKGROUND OF THE INVENTION

This invention relates generally to separation of particles from mixtures and, more specifically, to flow cytometers for analyzing and sorting biological particles.

Flow cytometry is a valuable method for the analysis and isolation of biological particles such as cells and constituent molecules. As such it has a wide range of diagnostic and therapeutic applications. The method utilizes a fluid stream to linearly segregate particles such that they can pass, single file, through a detection apparatus. Individual cells can be distinguished according to their location in the fluid stream and the presence of detectable markers. Thus, a flow cytometer can be used to produce a diagnostic profile of a population of biological particles. For example, flow cytometry has been used to measure the decline or maintenance of immune cells during the course of treatment for HIV infection and to determine the presence or absence of tumor cells for prognosis and diagnosis of cancer patients.

Isolation of biological particles has been achieved by adding a sorting or collection capability to flow cytometers. Particles in a segregated stream, detected as having one or more desired characteristics, are individually isolated from the sample stream by mechanical or electrical removal. This method of flow sorting has been used to separate sperm bearing X and Y chromosomes for animal breeding, to sort chromosomes for genetic analysis, to isolate cells bearing specific antigens and to identify new organisms from complex biological populations.

Biological particles isolated by flow sorting can be used for a variety of diagnostic or therapeutic applications. However, impurities that co-fracionate with a biological particle of interest in a flow sorting method can produce false results in a diagnostic assay or can have adverse consequences in a therapeutic procedure. Thus, flow sorting methods often require decontamination procedures to remove unwanted residual materials between sample applications. One method of decontaminating a flow system is to flush or purge the devices that come into contact with sample. Such methods can be time consuming and costly and are often incomplete.

Currently, flow cytometers are bulky instruments that occupy large amounts of valuable laboratory and clinic space. Reduction in flow cytometer size has previously come at the expense of functionality or performance. One approach that has been used to minimize the space required for flow cytometry has been to design the instruments to replace multiple components with alternative components that are interchangeable. For example, multilaser flow cytometers have been made more compact by replacing multiple lasers and their optical paths with a single optical path through which different lasers can be separately directed. In this format a single laser is used while alternative lasers can be omitted or stored at a separate location. A disadvantage of this approach is that interchanging components can be time consuming, thereby reducing the throughput of the instrument or precluding the full range of analyses available for a single sample.

Thus, there exists a need for a flow cytometer that can be efficiently decontaminated. A need also exists for a flow cytometer having a variety of functions available in a compact format. The present invention satisfies these needs and provides related advantages as well.

SUMMARY OF THE INVENTION

The invention provides an apparatus including (a) a frame having a boundary plane; (b) a flow chamber supported by the frame, the flow chamber placed a distance from the boundary plane; (c) a radiation source, the radiation source directed away from the flow chamber and away from the exterior side of the boundary plane, and (d) a first reflective surface placed to direct a radiation beam in a path crossing the boundary plane to the flow chamber; (e) one or more reflective surfaces placed to direct a radiation beam from the radiation source to the first reflective surface, the path from the radiation source to the flow chamber being at least 1.5 times the distance from the flow chamber to the boundary plane.

DETAILED DESCRIPTION OF THE INVENTION

Figure 1:
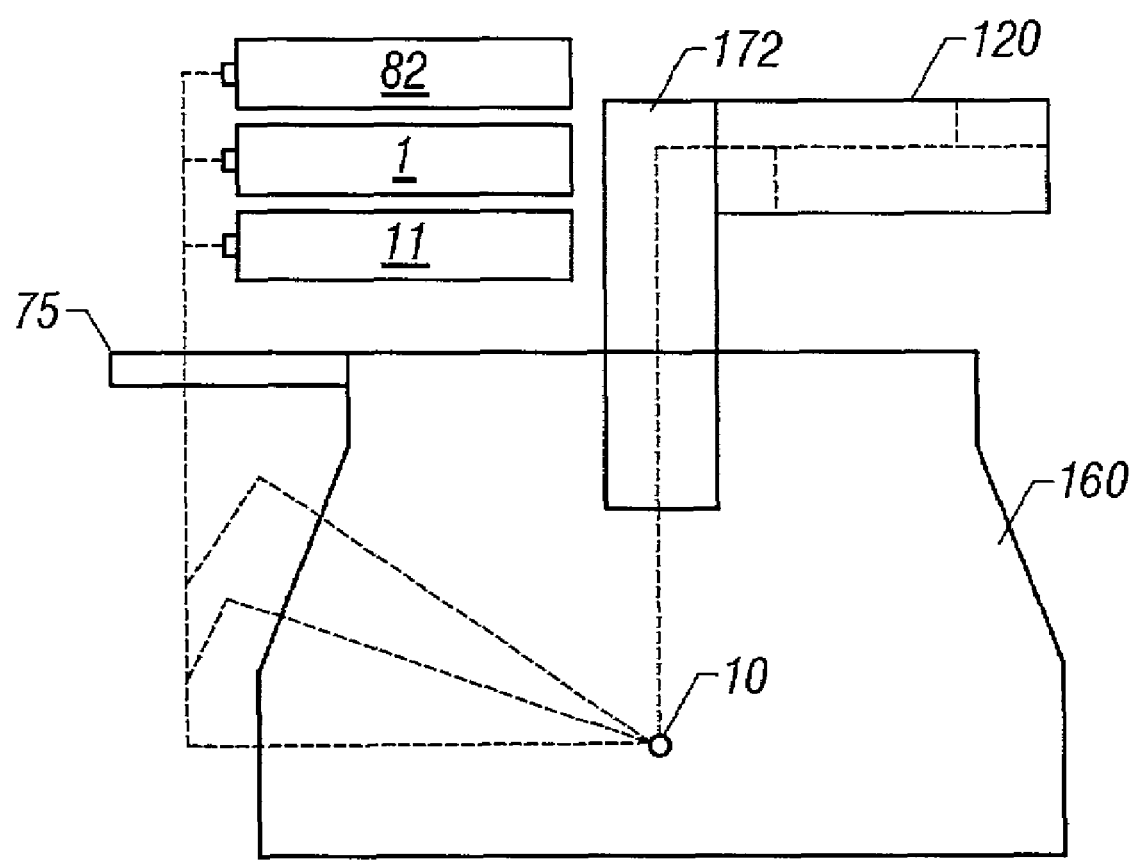
FIG. 1 shows a top view of a flow cytometer of the invention with 3 radiation sources.

This invention provides an apparatus for separating and sorting particles in a mixture. In one embodiment, an apparatus of the invention can be a flow cytometer for analyzing or sorting biological particles such as cells, organelles or macromolecules. An apparatus of the invention can include a rigid frame to which optical devices and flow system devices can be attached. Optical devices can be placed on the rigid frame of the instrument such that excitation radiation beam paths propagated from one or more radiation sources are folded within a compact volume prior to contacting a sample stream directed through a flow system to a flow chamber. Optical components can also be placed to direct two or more separate radiation beams from substantially parallel radiation sources to a flow chamber by directing the two or more radiation beams across the same boundary plane of a frame supporting the flow chamber. Parallel placement of two or more radiation sources provides the advantage of a compact volume occupied by the radiation sources. An emission radiation beam emitted can be directed from a flow chamber in a direction opposite an excitation radiation beam path, thereby folding excitation and emission beams in a "U" shaped path. By folding the paths for excitation and emission radiation beams, an apparatus of the invention can provide a compact format for analyzing and sorting particles in a mixture.

Radiation emitted from two or more locations in a sample stream can be directed as separate beams from a single lens to separate detectors located on the same side of the flow chamber. Thus, an apparatus of the invention can include a detector module removably connected detectors and filters for separate emission radiation beams. An advantage of a detector module having detectors and filters for multiple emission radiation beams located on the same side of a flow chamber is that the detectors can be located in a confined region of a flow cytometer, thereby providing manipulation without disturbing the function of other devices of a flow cytometer to which it is attached.

The invention further provides a detachable nozzle capable of attaching a sample tube such that the sample tube passes through an internal sheath fluid passageway and has a discharge end placed in or near the discharge opening of the nozzle. The nozzle can contain a shoe for removably connecting an oscillator. A nozzle of the invention can be made from disposable materials or materials that are resistant to particular decontamination procedures such as autoclaving. Thus, following use in a flow cytometer a nozzle of the invention can be rapidly and conveniently removed from both the flow cytometer and oscillator for disposal or separate decontamination procedure. An advantage of the nozzle design is that replacement or separate decontamination minimize sample carry over in a flow cytometer with which it is used.

An apparatus of the invention can include an adjustable bracket capable of removably connecting a nozzle. An adjustable bracket of the invention can be located on an exterior surface of the rigid optical frame, thereby providing convenient access for replacement of the nozzle. Additionally, the adjustable bracket can be placed to adjustably position the discharge opening of an attached nozzle such that a sample stream ejected from the nozzle can be directed to one or more excitation radiation beams.

The invention further provides a flow cytometer having a flow system in which all components that come into direct contact with a sample can be conveniently decontaminated by vacuum evacuation or removal and replacement. Specifically, the flow system includes a vacuum manifold having an internal channel with three openings. Two tubes can be attached to first and second openings of the manifold to form a continuous path from a sample container through the vacuum manifold internal chamber to a discharge opening in a nozzle. A third opening in the vacuum manifold can be attached to a vacuum source for evacuation of sample contents from the flow system. Furthermore, flow of a fluid in the tubing of the flow cytometer can be controlled by zero volume pinch valves. Zero volume pinch valves of the invention do not contact the sample and therefore need not be decontaminated between sample applications.

As used herein, the term "radiation beam" is intended to refer to a collection of electromagnetic waves or particles propagated in a uniform direction of propagation. The term is intended to include detectable collections of waves or particles having any energy in the electromagnetic spectrum. Examples of detectable collections of waves or particles include ultra violet (UV) radiation in the range of about 200 to 390 nm, visible (VIS) radiation in the range of about 390 to 770 nm, and infrared (IR) radiation in the range of about 0.77 to 25 microns. The term "excitation radiation beam" is intended to refer to a collection of electromagnetic waves or particles propagated in a uniform direction of propagation toward a flow chamber or sample stream. The term "emission radiation beam" is intended to refer to a collection of electromagnetic waves or particles produced by fluorescence and propagated in a uniform direction away from a flow chamber or sample stream.

As used herein, the term "direction," when used in reference to a radiation beam, is intended to refer to the axis along which the radiation beam is propagated. Accordingly, the terms "direct" and "directing," when used in reference to a radiation beam, refer to setting the axis along which a radiation beam is propagated. The axis along which a radiation beam is propagated can be set, for example, by aiming a radiation source, altering the angle of the axis along which a radiation beam propagates relative to a reference coordinate system such as by reflection, or by collimating radiation to form a beam.

As used herein, the term "boundary," when used in reference to a plane, is intended to mean a vertical plane that separates a radiation source from a flow chamber. An exterior side of a plane included in the term is opposite the side facing the flow chamber. The term can include, for example, a plane that is coincident with a surface of a flow cytometer or rigid frame thereof. A surface, when included in the term, can separate an internal chamber of a flow chamber from the exterior. The term can include, for example, a plane defined relative to two or more devices connected to the apparatus.

As used herein, the term "pin hole" is intended to mean a cavity that interrupts a screen, is surrounded on all sides by screen material and is transparent to UV, VIS or IR radiation. The term is intended to include a cavity containing any material transparent to irradiation in the UV, VIS or IR regions of the spectrum including, for example, air, glass, or quartz. The term can include, for example, a cavity extending through a metal layer of a mirror. A cavity in a mirror can contact a substrate of the mirror to which the metal layer is attached or can extend through the substrate. A cavity included in the term can contain a material that is selectively transparent to irradiation of a particular wavelength or wavelengths such as a filter material. The term can include a cavity having, for example, a width, diameter or major axis of about 2 mm or less, 1.5 mm or less, 1.0 mm or less, 0.5 mm or less, 0.2 mm or less, or 0.1 mm or less. A cavity included in the term can have any cross sectional shape including, for example, circular, elliptical, or square and can have uniform or non-uniform cross sectional dimensions along the axis that runs through the center of the cavity from the front to the back of the screen material. An example, of a cavity with uniform cross sectional dimensions along the axis that runs through the center of the cavity is a cylindrical pin hole. Alternatively, a cavity can have non-uniform cross sectional dimensions along the axis that runs through the cavity such as that of a conical cavity.

As used herein, the term "screen" is intended to mean any material that prohibits the passage of a photon or radiation. The term can include a mirrored surface on a transparent substrate including, for example, a metal layer on a glass or quartz substrate. A metal layer can include, for example, aluminum, silver, platinum or gold. The material can prohibit passage of radiation based on one or more properties of the radiation including, for example, wavelength, frequency, energy, polarization, intensity, beam width or incident direction. Thus, a screen can selectively pass a portion of the radiation contacting its surface. For example, a material can prohibit passage of radiation of a specific wavelength or range of wavelengths including, for example, radiation in the visible (VIS), ultraviolet (UV) or infrared (IR) regions of the spectrum.

As used herein, the term "mirrored," when used in reference to a surface, is intended to mean a surface that is sufficiently smooth to produce an image by specular reflection of radiation in the UV, VIS or IR regions of the spectrum. Specular reflection occurs when parallel rays of incident radiation, reflected according to the laws of reflection, are reflected parallel to each other at a surface. The laws of reflection hold that the angle of incidence is equal to the angle of reflection and the incident ray, reflected ray, and normal to the rays are coplanar. Diffuse reflection occurs when parallel incident rays are not parallel when reflected at a surface according to the laws of reflection, for example, due to irregularity in the surface.

As used herein, the term "flow chamber" is intended to mean a device that can produce or contain a sample stream and is transparent to UV, VIS or IR radiation. A sample stream can include any mobile phase that passes particles in single file including, for example, a fluid stream or fluid jet. The term is intended to include any particle including one or more molecules. A particle including one molecule can be, for example, a fluorophore or a macromolecule such as a polynucleotide, polypeptide, or other organic or biological polymer. A particle including more than one molecule can be, for example, a cell, molecular complex or bead.

As used herein, the term "flow cytometer" is intended to mean a device or apparatus having a means for aligning particles in a sample stream and a detector aligned such that the particles individually enter a zone of detection. A sample stream can include any mobile phase that passes particles in single file including, for example, a fluid stream or fluid jet. The term can include any particle including one or more molecules. A particle including one molecule can be, for example, a fluorophore or a macromolecule such as a polynucleotide, polypeptide, or other organic or biological polymer. A particle including more than one molecule can be, for example, a cell, molecular complex or bead.

As used herein, the term "radiation source" is intended to mean an origin or generator of propagated electromagnetic energy. The term can include any illumination sources including, for example, those producing electromagnetic radiation in the ultraviolet, visible and/or infrared regions of the spectrum. A radiation source can include, for example, a lamp such as an arc lamp or quartz halogen lamp, or a laser.

As used herein, the term "laser" is intended to mean a source of radiation produced by light amplification by stimulated emission of radiation. The term can include, for example, an ion laser such as argon ion or krypton ion laser, helium neon laser, helium cadmium laser, dye laser such as a rhodamine 6G laser, YAG laser or diode laser. These and other lasers useful in the apparatus of the invention are known in the art as described, for example, in Shapiro, *Practical Flow Cytometry*, 3$^{rd}$ Ed. Wiley-Liss, New York (1995).

As used herein, the term "discharge opening" is intended to refer to an end of a hollow tube or nozzle through which a fluid can exit. The term can include an end having an internal diameter of 1 mm or less, 0.5 mm or less, 0.3 mm or less, 0.1 mm or less or 0.05 mm or less.

As used herein, the term "pressure source" is intended to refer to an origin of positive displacement of a fluid or gas. The term can include, for example, positive displacement achieved by release of compressed gas or liquid or by gravity displacement. The term can also include positive displacement produced by a mechanical pump such as a syringe pump using a feed screw or rack and pinion drive.

As used herein, the term "oscillator" is intended to refer to a device capable of fluctuating its position at a constant frequency in response to applied energy. The term can include an electrically responsive element including, for example, a piezoelectric element or electromagnetic transducer.

As used herein, the term "lens" is intended to refer to a transparent material having a refractive index greater than that of air with opposite surfaces either or both of which are curved. The term can include a gradient index lens, concave lens, convex lens, Fresnel lens, gradient index lens, concave mirror or cylindrical lens.

As used herein, the term "reflective," when used in reference to a surface is intended to mean a surface that is able to redirect a radiation beam in the UV, VIS or IR regions of the spectrum such that the angle of incidence is equal to the angle of reflection where the incident beam, reflected beam, and normal to the beams are coplanar. The term can include, for example, an internal surface of a transparent material such as a surface of a prism, a surface formed at the interface of two materials such as metal coated glass or metal coated quartz or the exterior surface of a polished material such metal or plastic. Examples of metals that can form a mirror when coated on glass or quartz or when polished include aluminum, silver, platinum or gold.

As used herein, the term "detector" is intended to mean a device or apparatus that converts the energy of contacted photons into an electrical response. Th term can include an apparatus that produces an electric current in response to impinging photons such as in a photodiode or photomultiplier tube. A signal detector can also accumulate charge in response to impinging photons and can include, for example a charge coupled device.

As used herein, the term "filter cassette" is intended to mean a frame attached to a device for selectively passing or rejecting passage of radiation in a wavelength, polarization or frequency dependent manner. The term can include a frame that is additionally attached to a radiation detecting device or to an attachment module. The term can also include a frame that is removably attached to a device for selectively passing or rejecting radiation, a radiation detecting device or an attachment module.

As used herein, the term "optical filter" is intended to mean a device for selectively passing or rejecting passage of radiation in a wavelength, polarization or frequency dependent manner. The term can include an interference filter in which multiple layers of dielectric materials pass or reflect radiation according to constructive or destructive interference between reflections from the various layers. Interference filters are also referred to in the art as dichroic filters, or dielectric filters. The term can include an absorptive filter which prevents passage of radiation having a selective wavelength or wavelength range by absorption. Absorptive filters include, for example, colored glass or liquid.

A filter used in the invention can have one or more particular filter transmission characteristics including, for example, bandpass, short pass and long pass. A band pass filter selectively passes radiation in a wavelength range defined by a center wavelength of maximum radiation transmission ($T_{max}$) and a bandwidth and blocks passage of radiation outside of this range. $T_{max}$ defines the percentage of radiation transmitted at the center wavelength. The bandwidth is typically described as the full width at half maximum (FWHM) which is the range of wavelengths passed by the filter at a transmission value that is half of $T_{max}$. A band pass filter useful in the invention can have a FWHM of 10 nanometers (nm), 20 nm, 30 nm, 40 nm or 50 nm. A long pass filter selectively passes higher wavelength radiation as defined by a $T_{max}$ and a cut on wavelength. The cut on wavelength is the wavelength at which radiation transmission is half of $T_{max}$, and as wavelength increases above the cut on wavelength transmission percentage increases and as wavelength decreases below the cut on wavelength transmission percentage decreases. A short pass filter selectively passes lower wavelength radiation as defined by a $T_{max}$ and a cut off wavelength. The cut off wavelength is the wavelength at which radiation transmission is half of $T_{max}$ and as wavelength increases above the cut off wavelength transmission percentage decreases and as wavelength decreases below the cut off wavelength transmission percentage increases. A filter of the invention can have a $T_{max}$ of 50-100%, 60-90% or 70-80%.

As used herein, the term "scattered," when used in reference to radiation, is intended to mean radiation that is directed from an irradiated molecule or particle, and having the same wavelength as the irradiating radiation. The term can include "large angle scattered radiation" which refers to radiation directed from an irradiated molecule or particle at an angle of 15°-150° from the direction of incident irradiation. The term can include "orthogonal scattered radiation" which refers to radiation directed from an irradiated molecule or particle at an angle of about 90° from the direction of incident irradiation. The term can also include "small angle scattered radiation" which refers to radiation directed from an irradiated molecule or particle at an angle of 0.5°-5° from the direction of incident irradiation. Small angle scattered radiation is also referred to in the art as forward scatter.

As used herein, the term "manifold" is intended to mean a body having an internal cavity with three or more openings to an external surface. The term can include an extended channel having an opening at each end and contacted internally by a second channel having an opening at an end opposite the contacting end. The term can include a "vacuum manifold" which further refers to a body having sufficient strength to support a cavity evacuated by a vacuum. A vacuum included in the term can provide a differential pressure of at least 100 torr, at least 200 torr, or at least 300 torr.

As used herein, the term "seal" is intended to mean a closure forming an airtight connection with a container. A seal can be made of any material capable of making an airtight connection with a glass or plastic container including, for example, rubber, TYGON® or silicone.

As used herein, the term "vacuum source" is intended to mean an origin of reduced air pressure. The term can include a mechanical vacuum pump.

As used herein, the term "zero volume pinch valve" is intended to mean a device that compresses a tube by application of force on an external surface of the tube with sufficient effect to reduce or prevent passage of a liquid or gas through the tube. The term can include, for example, a screw clamp, spring clamp or vise.

The invention provides an apparatus including (a) a frame having a boundary plane; (b) a flow chamber supported by the frame, the flow chamber placed a distance from the boundary plane; (c) a radiation source, the radiation source directed away from the flow chamber and away from the exterior side of the boundary plane, and (d) a first reflective surface placed to direct a radiation beam in a path crossing the boundary plane to the flow chamber; (e) one or more reflective surfaces placed to direct a radiation beam from the radiation source to the first reflective surface, the path from the radiation source to the flow chamber being at least 1.5 times the distance from the flow chamber to the boundary plane.

The invention further provides an apparatus including (a) a flow chamber; (b) a first reflective surface placed to direct an excitation radiation beam to the flow chamber; (c) one or more devices for directing an excitation radiation beam to the first reflective surface, wherein the excitation radiation beam passes orthogonally through a vertical plane in a forward direction, and (d) a device for directing an emission radiation beam from the flow chamber, wherein the emission radiation beam passes through the vertical plane in a reverse direction compared to the forward direction.

The invention further provides an apparatus including (a) a flow chamber capable of being contacted by a radiation beam; (b) a reflective surface, wherein the reflective surface is responsive to radiation in the UV, VIS and IR regions of the spectrum; (c) a lens placed to direct a radiation beam from the flow chamber to the reflective surface; (d) a detector module; (e) a second reflective surface placed to reflect the radiation beam from the reflective surface to the detector module, wherein the reflective surface is responsive to radiation in the UV, VIS and IR regions of the spectrum, and (f) a detector removably connected to the detector module, wherein the detector is placed to detect the radiation beam.

The invention further provides an apparatus including (a) a flow chamber having two separate points capable of being contacted by separate radiation beams; (b) a detector module; (c) a lens placed to direct separate radiation beams from the two separate points to the detector module; (d) a first detector removably connected to the detector module, wherein the first detector is placed to detect the first radiation beam, and (e) a second detector removably connected to the detector module, the second detector being placed to detect the second radiation beam, wherein the first and second detectors are placed on the same side of the first and second radiation beams directed from the lens to the first pair of reflective surfaces.

An apparatus of the invention can be a flow cytometer as described further below. Although the full range of apparatus encompassed within the invention is limited only by the claims, the embodiments shown in the Figures are used here as examples to illustrate features of the device. The invention provides a flow cytometer having one or more radiation sources directed away from an exterior side of a boundary plane and away from a flow chamber of the flow cytometer. FIG. 1 shows a top view of a flow cytometer frame and 3 radiation sources, with superimposed excitation and emission radiation beam paths. Radiation source 1, radiation source 11 and radiation source 82 can be directed away from boundary plane 75 and away from flow chamber 10 as shown in FIG. 1. As shown by the superimposed beam paths, the excitation beams from each radiation source can be folded to cross boundary plane 75 and contact flow chamber 10. It is understood that a variety of beam paths can be utilized in a flow cytometer of the invention to achieve the above-described orientation of radiation source and flow cytometer. Examples of such beam paths and radiation directing devices useful in achieving these paths are described below.

Figure 2:
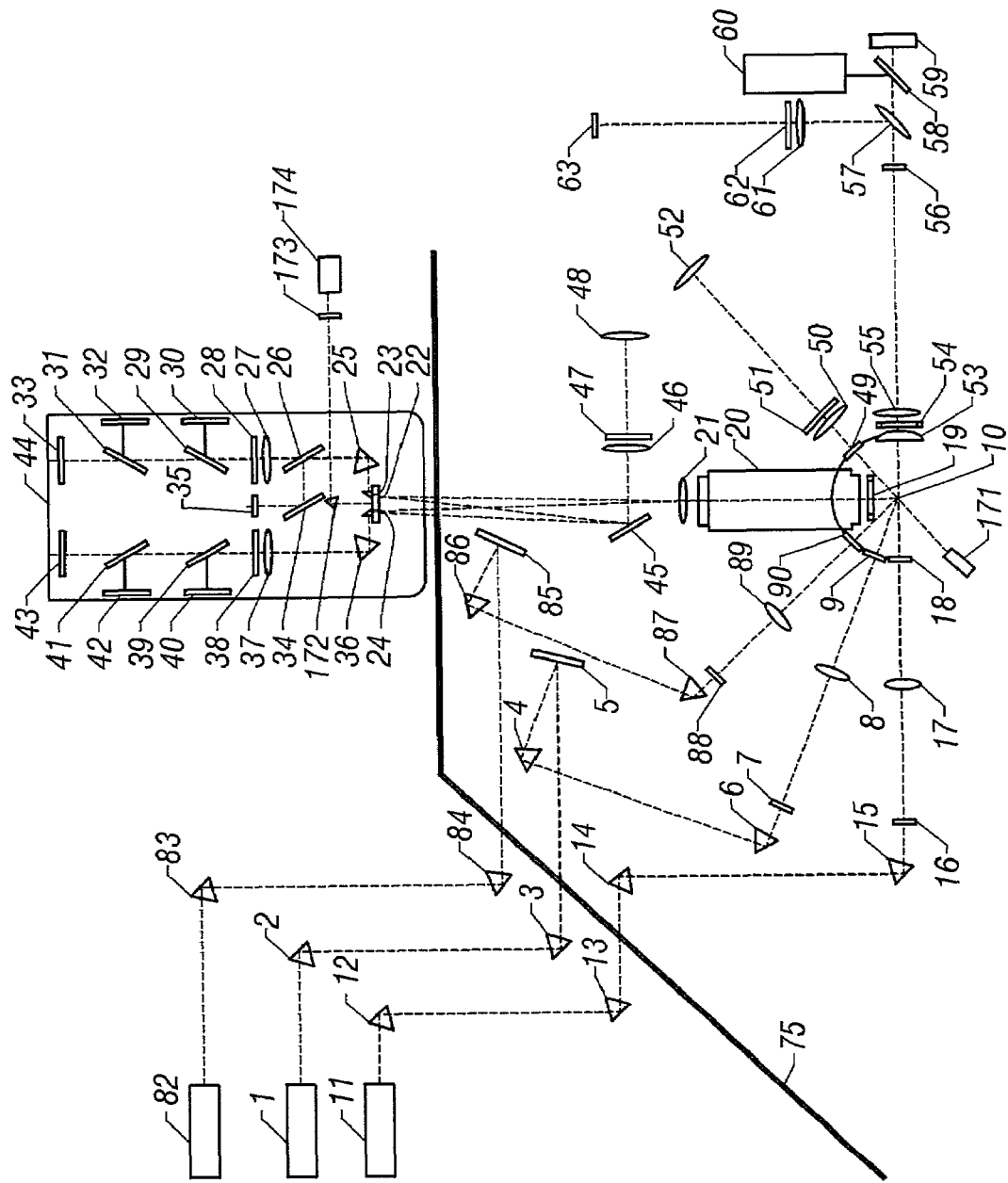
FIG. 2 shows a two dimensional diagram of optical devices for directing radiation in a flow cytometer.

FIG. 2 provides a schematic view, in two dimensions, of an embodiment of the invention having compact optical paths for up to 3 radiation beams. A first radiation source 11, such as a laser, can be placed to direct an excitation radiation beam along a reflected path by a series of reflective surfaces to a flow chamber 10. A radiation beam emitted from radiation source 11 can be directed horizontally to prism 12 which can be placed to reflect the beam orthogonally in a vertical direction to prism 13 which can in turn reflect the radiation beam orthogonally to prism 14 in a direction that is horizontal and perpendicular to the direction of the radiation beam propagated from radiation source 11 to prism 12. Prism 14 can be placed to reflect a radiation beam orthogonally in a vertical direction to prism 15. Prism 15 can be placed to reflect an incident radiation beam orthogonally in a horizontal direction and through an iris diaphragm 16 to lens 17. An iris diaphragm can be used to align a radiation beam and can be adjusted to have different size apertures for passage of beams having different cross sectional shapes or diameters. An iris diaphragm useful in the invention can include, for example, diaphragm SM1D12 from Thorlabs, Newton, N.J. Lens 17 can be placed to focus the radiation beam to pass through a window 18 to contact a sample stream passing through a flow chamber 10.

The invention provides a flow chamber that can be sealed to prevent undesirable escape of fluid samples while having one or more window for entry of excitation radiation beams. For example, window 18 can be placed to seal flow chamber 10 to prevent liquid contents of flow chamber 10 from contacting optical components. A flow chamber included in a flow cytometer of the invention can further include windows that can be sealed while allowing exit of emission and scatter radiation, as described below. Thus, a flow cytometer of the invention provides the advantages of protecting optical components and users from making unwanted contact with fluid samples.

Figure 3:
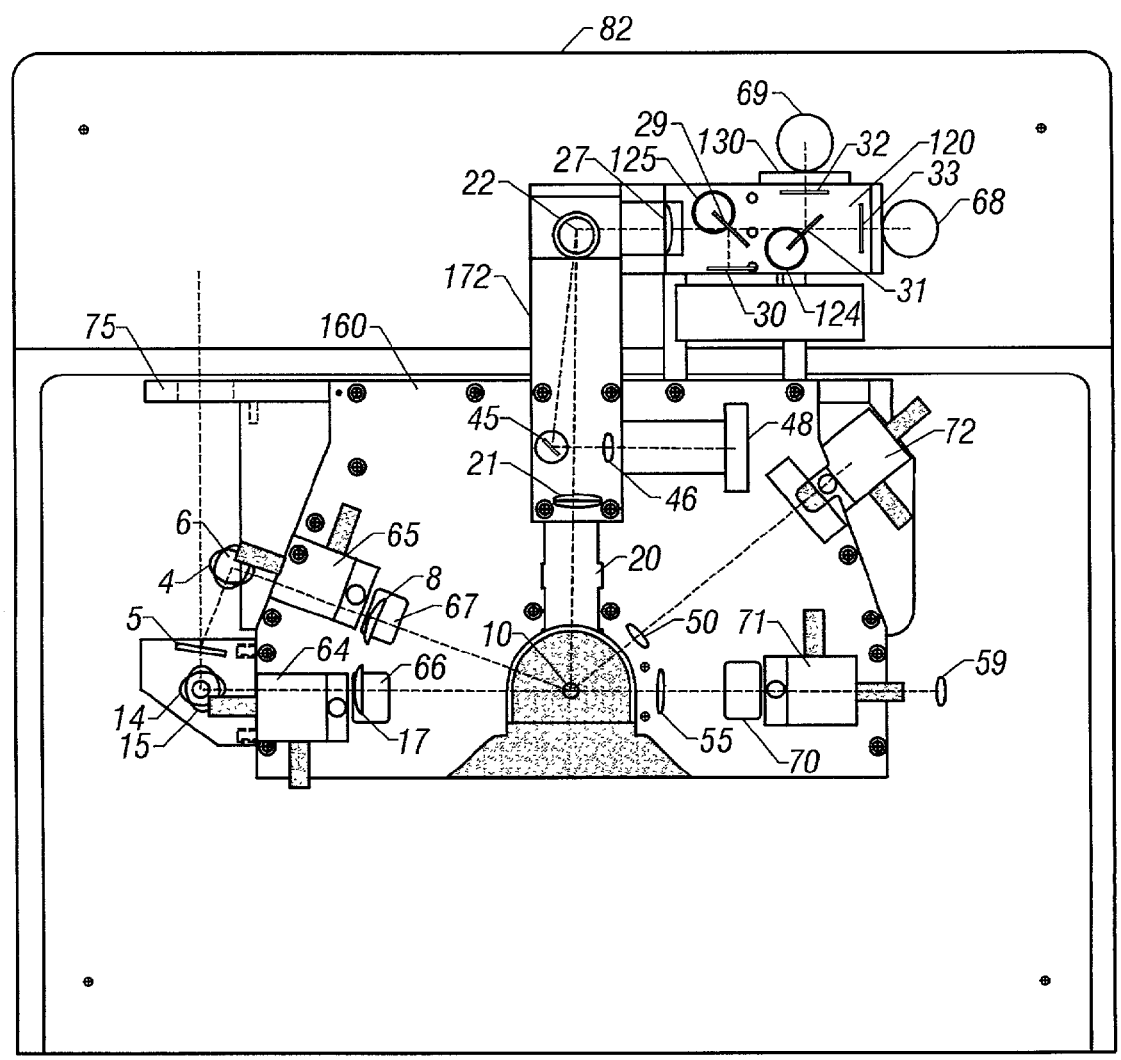
FIG. 3 shows a top view of a flow cytometer of the invention.
Figure 4:
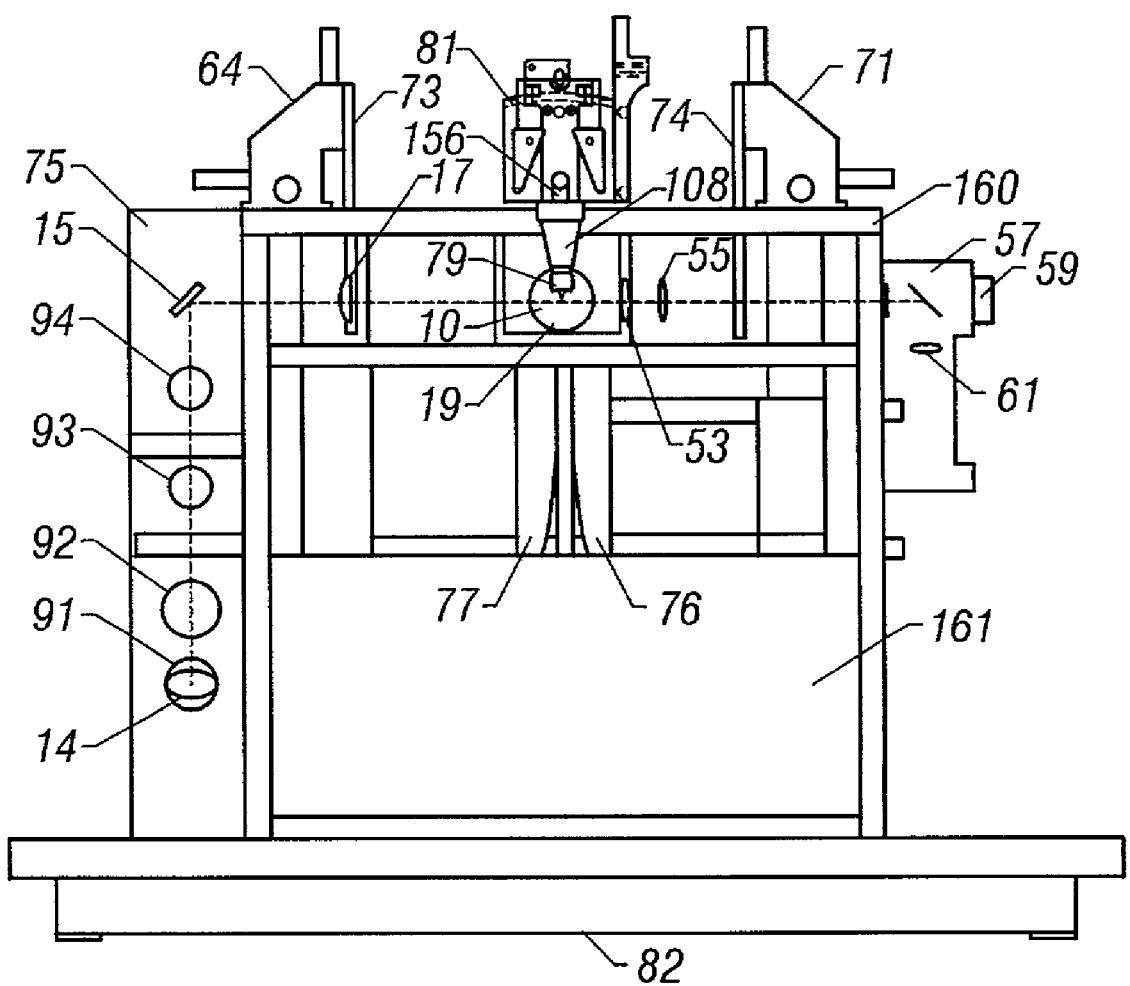
FIG. 4 shows a side view of a flow cytometer of the invention.

An excitation radiation beam path can pass through vertical and horizontal planes of the instrument as shown, for example, by comparison of top and side views of a flow cytometer of the invention in FIGS. 2 and 3, respectively. For example, as shown in FIG. 3, an excitation radiation beam can pass a vertical rear boundary plane 75 of the instrument as well as a vertical side boundary plane separating prisms 14 and 15 from flow chamber 10 and separating prism 4, prism 6 and reflector 5 from flow chamber 10. As shown in FIG. 4, an excitation radiation beam can cross a horizontal plane when directed from prism 14 to prism 15. As used herein, a vertical or horizontal plane can be coincident with a surface of an apparatus of the invention or can be defined relative to two or more devices connected to the apparatus.

An apparatus of the invention can provide independent control and adjustment of alignment for separate excitation radiation beams. A steering device 64 can be functionally connected to lens 17 to provide adjustment of the direction or focus of an excitation radiation beam. Lens 17 can be adjusted to align an excitation radiation beam for passage through field stop 18, thereby providing alignment of the excitation beam with a flow chamber and detection optics of a flow cytometer. The aperture of window 18 can be selected so as to reject passage of misaligned radiation or to reduce detection of stray radiation by the detection optics. Steering device 64 can be placed on an exterior surface 160 of a flow cytometer frame to provide convenient manipulation and adjustment without the need to enter a chamber containing the radiation beam path. Separation of steering device from the radiation beam path chamber can be achieved with an extension arm 73 connecting lens 17 and passing through a hole 66 in the frame. As described below, a flow cytometer of the invention can further include a separate lens 8 for focusing or aligning a separate radiation beam relative to a separate field stop 9. A separate steering device, can be functionally connected to lens 8, thereby providing independent adjustment of alignment for separate radiation beams of a flow cytometer of the invention.

An apparatus of the invention can provide detection of emitted or scattered radiation intensity that is independent of anisotropic radiation emission. A radiation source used in an apparatus of the invention can produce polarized radiation. The intensity of radiation scatter and emission for a particle irradiated with polarized radiation is generally dependent on the angle of detection and the degree of anisotropy of the radiation emitted or scattered by the particle. However, intensity of scattered and emitted radiation is independent of anisotropic radiation emission when detected at an angle of about 54.7° from the direction of the excitation polarization.

An apparatus of the invention can include detection of scattered and emitted radiation at an angle of about 54.7° from the direction of the excitation polarization to provide detection that is independent of intensity variations due to anisotropic radiation emission. A radiation source, flow chamber, detector and intervening reflective surfaces or beam directing devices included in an apparatus of the invention can be oriented such that detection occurs at an angle of about 54.7° from the direction of the excitation polarization. One skilled in the art will be able to use well known geometric principles and known properties of optical components to determine appropriate orientation of optical components for detection that is independent of intensity variations due to anisotropic radiation emission. Anisotropic-independent detection can be achieved using methods known in the art as described, for example, in Asbury et al., *Cytometry* 40:88-101 (2000), which is incorporated herein by reference.

A second radiation source 1 can be included in a flow cytometer of the invention. As shown in FIG. 2, radiation source 1 can be placed to emit a radiation beam parallel to a radiation beam emitted from radiation source 11. An excitation radiation beam originating from source 1 can be directed to the same side of a flow cytometer as radiation source 11, such that both excitation radiation beams cross the same boundary plane of the apparatus along different reflected paths to a flow chamber 10. Reflective surfaces in a second excitation radiation beam path can include prism 2 placed to reflect a horizontal beam from radiation source 1 to prism 3 along a vertical path. Prism 3 can be placed to reflect a radiation beam to reflective surface 5 in a direction that is horizontal and perpendicular to the direction of the radiation beam propagated from radiation source 1 to prism 2. Reflective surface 5 can be, for example, a mirror or interference filter and can be placed to reflect a radiation beam from prism 3 to prism 4 at an angle of about 20° in a horizontal plane. Prism 4 can reflect a radiation beam orthogonally in a vertical direction to prism 6, which can be placed to reflect a beam orthogonally in a horizontal direction through iris diaphragm 7 to lens 8. As described above, lens 8 can be placed to focus or align a radiation beam to pass through a window 9 to contact a sample stream passing through a flow chamber 10.

As further shown in FIG. 2, an apparatus of the invention can have a third radiation source 82 that can be placed to emit a radiation beam parallel to a radiation beam emitted from radiation source 11 and radiation source 1. Parallel placement of radiation sources can provide compact placement. For example, lasers can be bulky and, when arrayed at different angles, can occupy a large amount of space, whereas parallel placement of the lasers, such as by stacking or side by side placement, can reduce the space occupied by three lasers. As shown in FIGS. 2 and 3, separate radiation beams can enter a back plane 75 of a flow cytometer of the invention at different elevations, for example, through vertically aligned openings 91, 92, 93 or 94. Entry of separate beams at different elevations can provide compact placement of lasers, for example, by stacking. Alternatively, reflective surfaces can be placed at different elevations to direct radiation beams from a single level through vertically aligned openings in a flow cytometer.

An excitation radiation beam originating from source 82 can be directed to the same side of a flow cytometer as radiation source 1 and radiation source 11, such that the three excitation radiation beams cross the same boundary plane of the apparatus. Thus, separate radiation beams can enter flow chamber 10 from the same side, for example, within a 45° arc. Separate radiation beams propagating from parallel radiation sources can enter the flow chamber from different angles as determined by the placement of reflective surfaces. For example, beams propagating from radiation source 1 and radiation source 11, although initially parallel and following similar paths of orthogonal reflection, differ in angle of flow chamber contact due to the addition of reflective surface 5 in the radiation beam path of the former. Similarly, beams propagating from radiation source 1 and radiation source 82 differ in angle of flow chamber contact due to the different angles at which reflective surface 5 and reflective surface 85 are placed.

A radiation beam propagating from source 82 can be reflected orthogonally by prism 83 vertically to prism 84, which can in turn reflect the radiation beam orthogonally along a horizontal path to reflective surface 85. Reflective surface 85 can be placed to reflect a radiation beam from prism 84 to prism 86 at an angle of about 40° in a horizontal plane. Prism 86 can reflect a radiation beam orthogonally in a vertical direction to prism 87, which can be placed to reflect a beam orthogonally in a horizontal direction through iris diaphragm 88 to lens 89. Lens 89 can be placed to focus or align a radiation beam to pass through a window 90 to contact a sample stream passing through a flow chamber 10.

Placement of a radiation source such that it is directed away from a boundary plane and flow chamber provides a compact placement of a flow cytometer and radiation source. This compact placement can be provided by folding the excitation radiation beam into an elongated path compared to a path leading directly from the boundary plane to the flow chamber. The type of optical devices used in an optical path of the invention and their placement can also be selected to provide detection at an anisotropic-independent angle as described above. The exemplary paths described above provide both a compact format for the cytometer and detection at an anisotropic-independent angle. Accordingly, the exemplified paths are longer than 1.5 times the distance from flow chamber 10 to boundary plane 75. A variety of excitation beam paths can be incorporated to achieve compact placement of a radiation source with respect to a flow cytometer and detection at an anisotropically-independent angle. Depending upon the placement of optical devices such as prisms and reflective surfaces, the resulting beam paths can have different lengths including, for example, a path that is at least 2 times the distance from a flow chamber to a boundary plane, at least 2.5 times the distance from a flow chamber to a boundary plane, or at least 3 times the distance from a flow chamber to a boundary plane.

The compact design of the flow cytometer can be further achieved by the directing one or more emission beams from a flow chamber to various detectors located on the same side of the flow chamber. Two or more radiation beams can be directed from separate points in a sample stream contained in a flow chamber to a single side of a flow chamber by a single lens. By directing multiple emission radiation beams to the same side of a flow chamber, the invention allows multiple detectors to be placed in a single detector module. The compact format provided by the excitation and emission radiation beam paths of the invention provide a flow cytometer that can be contained within a compact area including, for example, an area having dimensions of 15 inches by 9 inches or smaller.

As shown in FIG. 2, emission from two or more locations in a sample stream located within the flow chamber 10 can pass through a scatter bar 19 that is positioned to block excitation radiation that is reflected off the surface of the jet. Emitted radiation can be collected by a lens 20 and collated by a lens 21 such that two or more radiation beams can be directed to a screen 22 having a mirrored surface and one or more pin holes. Proper alignment of the optical components will allow a radiation beam to pass through a pin hole in screen 22 to contact a detector. As shown in FIG. 2, two properly aligned excitation radiation beams can pass through the pin holes to contact prisms 24 and 23 which can be attached to the opposite side of screen 22. As described below, the mirrored surface prevents passage of misaligned radiation and can be used to determine the trajectory or focus of a misaligned radiation beam. Prisms 24 and 23 can be placed to reflect aligned radiation beams to diverge in opposite directions toward prisms 25 and 36, respectively. Prisms 25 and 36 can be placed to reflect the divergent beams parallel to each other and in the same direction.

Emission radiation beams propagating from separate locations of a flow chamber can be directed in parallel trajectories to enter a detector module from the same side. Detectors can be connected to the detector module and the parallel emission beams directed to the attached detectors by reflective surfaces and filters also connected to the detector module. A radiation beam reflected from prism 36 can be directed to lens 37 which can be a 75 mm lens placed to collimate and direct the radiation beam through optical filter 38 to dichroic beam splitter 39. Dichroic beam splitter 39 can be a type that reflects radiation from about 510 to 540 nm while passing radiation to detector 40 and passes longer wavelength radiation to dichroic beam splitter 41. Dichroic beam splitter 41 can be of the type that reflects radiation shorter than 600 nm to detector 42 and passes longer wavelength radiation to detector 43. As shown for the radiation beam path directed from prism 25, an additional beam splitter 26 can be placed to reflect a fraction of the radiation to reflective surface 34 which reflects the radiation beam to detector 35. A radiation beam passing through dichroic beam splitter 26 can be directed by lens 27 through optical filter 28 to dichroic beam splitter 29. Dichroic beam splitter 29 can be of the type that reflects radiation shorter than 450 nm to detector 30 and passes longer wavelength radiation to dichroic beam splitter 31. Dichroic beam splitter 31 can be of the type that reflects 500 nm radiation to detector 32 and passes longer wavelength radiation to detector 33.

The optical components in an emission beam path of a flow cytometer of the invention can be replaced or altered from those exemplified above to accommodate different conditions including, for example, different excitation sources, different fluorescent dyes to be detected, or different detectors. For example, a dichroic beam splitter or combination of dichroic beam splitters can be selected based on cut-off or cut-on wavelengths and the effectiveness with which they can separate emission from a particular set of dyes in a sample. Those skilled in the art will know or be able to determine appropriate dichroic beam splitters for use in a flow cytometer of the invention as described, for example, in Shapiro (1995), supra. Beam splitters and their properties are known in the art and can be obtained from commercial sources including, for example, Melles Groit (Irvine, Calif.), or Oriel Corp. (Stratford, Conn.). As described below, the invention provides removable attachment of optical components of the emission beam path to a detector module, thereby providing rapid and convenient replacement or adjustment to suit a variety of desired applications.

The invention provides detection of perpendicular scatter that has been directed through the same lens that directs emission radiation from a flow chamber. As shown in FIG.

2, a perpendicular scatter detector 35 can be placed to detect radiation reflected from dichroic beam splitter 26. Alternatively, the invention provides detection of perpendicular scatter that has been directed through the same lens that directs emission radiation from a flow chamber and prior to being filtered by devices in the emission radiation beam path. As shown in FIG. 2, a perpendicular scatter detector 174 can be placed to detect radiation that passes through a separate pin hole in screen 22. As described below with regard to forward scattered radiation, the size of the pin hole and its distance from the flow chamber can be selected to limit the angle of perpendicular scatter that reaches detector 174. The perpendicularly scattered radiation that passes through a pin hole can be reflected by prism 172 to pass through a filter 173 prior to contacting detector 174.

A detector module of the invention can be placed such that a detector for a first emission radiation beam and detector for a second emission radiation beam propagated from a flow chamber by a single lens occur on the same side of the flow chamber. An advantage of placing detectors on one side of a flow chamber is that a more compact apparatus is provided compared to that which is available when two emission radiation beams are directed from a flow chamber in opposite directions to detectors placed at different locations. A detector module of the invention can be placed exterior to a frame or housing of a flow cytometer providing convenient access to detectors and filters. Thus, detectors and filters can be aligned, replaced, or otherwise manipulated without disturbing operation of other components of the instrument such as the flow system or excitation optics.

Figure 5A:
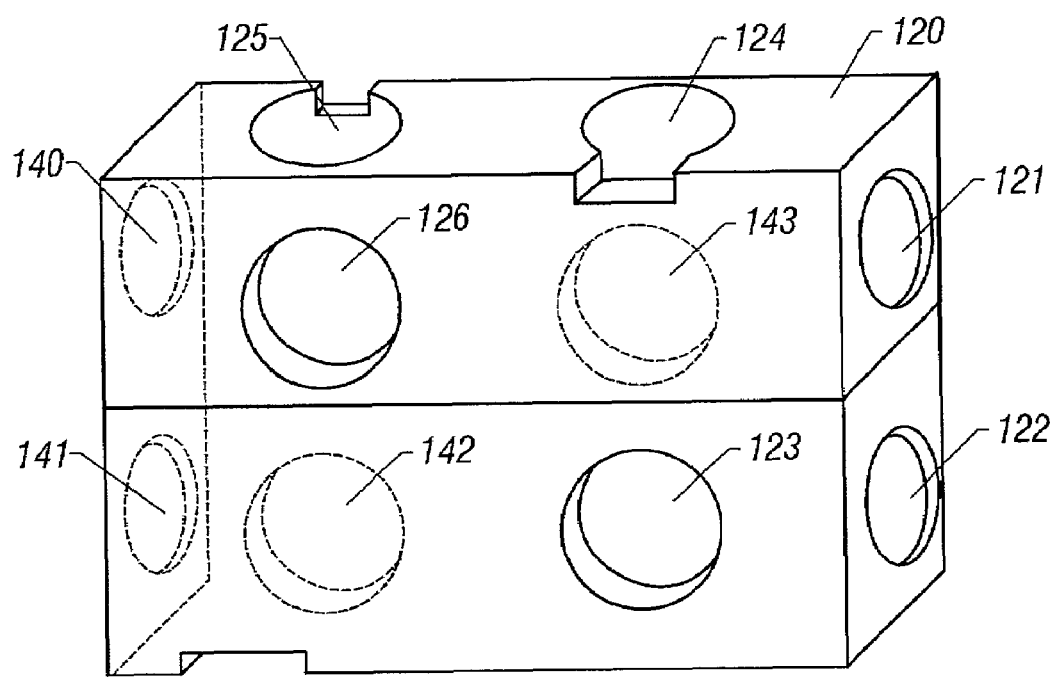
FIG. 5 shows a detector module in part A and an exploded view of an attachment module with filter cassette and detector in part B.
Figure 5B:
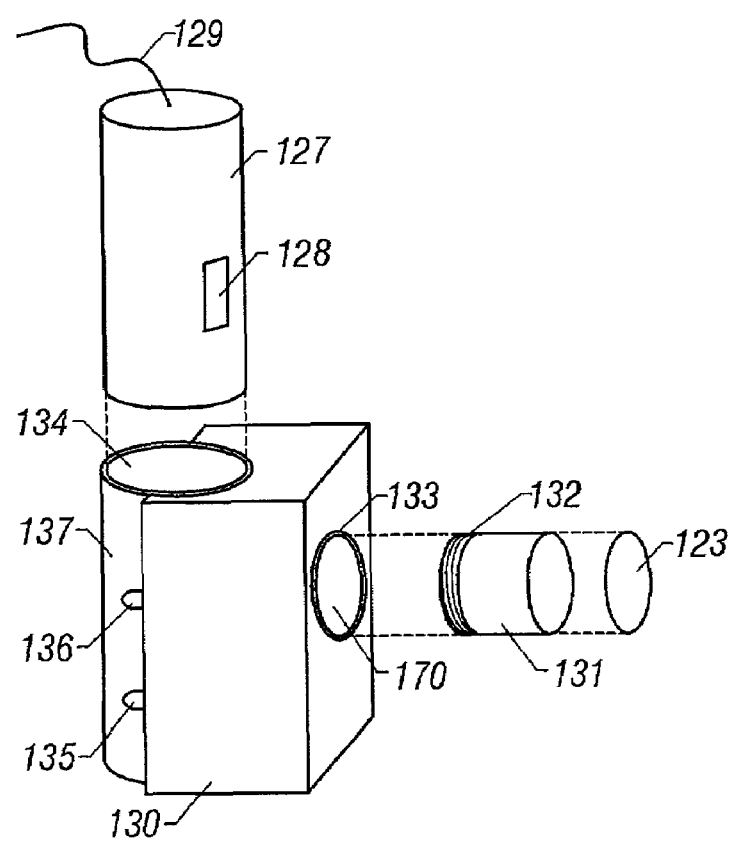

An exploded view of a detector module 120 is shown in FIG. 5. Detector module 120 provides a rigid frame having an elongated cavity accessible to an emission radiation beam by multiple openings. A radiation beam can be directed through the cavity by entry through opening 140 and can exit through oppositely placed opening 121. Detector module 120 can include a cavity capable of passing a separate radiation beam propagating parallel to a beam entering opening 140. A separate beam can enter the detector module through an opening 141 located on the same face as opening 140. A detector module can additionally include an opening 126 placed orthogonal to entry opening 121 through which reflected radiation can exit the detector module. One or more additional exit openings can be placed between and orthogonal to entry opening 140 and exit opening 121 including, for example, exit opening 143. Similarly, a parallel radiation beam entering opening 141 can exit directly through opening 122 or can be reflected through orthogonal opening 142 or orthogonal opening 123.

An access opening 125 can be placed proximal to an orthogonal opening 126 to provide placement or adjustment of a beam splitter or reflective surface. Each orthogonal opening can have a separate access opening such that individual beam splitters or reflective surfaces can be attached to separate adjusting devices for independent control of each. Separate access openings can also allow convenient replacement of an individual optical component without disturbing other components of the detector module. In addition to providing individual access and adjustment of optical components, a detector module of the invention being made of a rigid material such as aluminum, can restrict the degree of freedom between attached optical components. Thus, adjustment of one component is unlikely to alter the position of other components so long as the position of the detector module itself is not altered.

Each exit opening in a detector module of the invention can be removably attached to a separate detector. As shown in FIG. 5, a detector 69 can be removably attached to an attachment module 130 by a clamp 137 compressed to the body of the attachment module by pressure supplied, for example, by one or more screws 135. Detector 69 can be placed in attachment module 130 such that a radiation detecting surface 128 faces an opening 143. A cassette 131 having an internal cavity open at two ends can be attached at one end to detector module 130 at opening 143. The other end of cassette 131 can be attached to an exit opening of detector module 120, for example, exit opening 123. Accordingly, a radiation beam directed into a detector module 120 can pass through an exit opening 123, cassette 131, and attachment module 130 to reach a detecting surface 128. Cassette 131 can be removably attached to detector module 120 and attachment module 130. For example, contact can occur by screw thread attachment 132. Alternatively, a cylindrical shaped cassette 131 can be fit into a round opening and held in place by friction such as that provided by an O-ring wrapped around the cassette and contacting the sides of the opening.

Cassette 131 can also be removably attached to an optical filter. Thus, a cassette can provide spectrum selective passage of radiation to detector 69. An optical filter can be removably attached to an internal surface of cassette 131. For example, the internal surface of cassette 131 can be threaded and a filter can be held in place by compression between to rings screwed into the inner threads of cassette 131.

A flow cytometer of the invention can include a device to detect forward scatter, orthogonal scatter or both. Orthogonal scatter can be collected by the same lens 20 that collects emission radiation and directed to an orthogonal scatter detector 35 as described above. As shown in FIG. 2, a detector 60 can be placed to detect forward scattered radiation produced from an irradiated particle in flow chamber 10. Scattered radiation can be directed from flow chamber 10 by one or more lens including, for example Lens 53 and lens 55. A scatter bar 54 can be placed between flow chamber 10 and detector 60 to prevent radiation reflected from the surface of the jet from reaching detector 60 while allowing radiaiton scattered from particles contained inside the jet to reach the detector.

An iris diaphragm 56 can be placed between flow chamber 10 and detector 60 to limit the angle of forward scattered radiation observed. The distance between field stop 56 and flow chamber 10 or the size of the opening in field stop 56 can be altered to change the maximum angle of scattered radiation reaching detector 60. For example, an opening that passes radiation at an angle of 3° or less can be moved closer to flow chamber 10 to pass radiation at an angle of 1° or less or even 0.5° or less. Alternatively, the size of the opening can be increased to pass radiation at a higher maximum angle including for example 5° or less. The intensity of forward scattered radiation that contacts detector 60 can be controlled by a beam splitter 58 placed to reflect a fraction of incident light toward detector 60. Radiation passing through beam splitter 58 can be directed to a bar alignment window 59. The window can project an image of a nozzle tip and scatter bar and the relative position of the two images can be used to determine alignment of the flow system and optical system of the flow cytometer.

The invention further provides a device for determining alignment of a radiation beam in a flow cytometer. As described above, screen 22 can have one or more pin holes for passage of one or more properly aligned radiation beams. Screen 22 can additionally have a mirrored surface. The mirrored surface can provide accurate identification of a misaligned radiation beam and its location relative to the pin hole while simultaneously providing observation of the sample and the point at which the sample is contacted by a radiation beam. Specifically, the location or shape of a radiation beam's reflection on the mirrored surface can be correlated with direction of propagation or focus of an emission radiation beam and can be used to guide in adjusting optical components of the apparatus to achieve proper alignment. Additionally, alignment of a sample stream and excitation radiation beam can be determined from an image reflected on the mirrored surface.

A camera 48 can be placed to observe the mirrored surface of screen 22 for simultaneous determination of alignment for an excitation radiation beam and emission radiation beam relative to a sample stream. As shown in FIG. 2, an image of a misaligned radiation beam and sample stream can be reflected to camera 48 by a help mirror 45. A help mirror 45 can be included in an apparatus of the invention to reflect an image from screen 22 away from an emission radiation beam path so that a detection camera does not interfere with the emission beam. A lens 46 can be placed to focus an image reflected from screen 22 to camera 48. Additionally, a filter 47 can be placed to block excitation radiation beams from reaching camera 48 to a camera 48.

A screen of the invention can consist of any material that is capable of substantially blocking passage of a photon and that can be coated with or otherwise attached to a reflective surface. Depending upon the material used, the screen can block photons in a particular region of the spectrum including, for example, visible, ultraviolet, or infrared regions. One skilled in the art will be able to determine an appropriate screen material for use in the invention according to the range of radiation that is desired to be blocked. Examples of materials that can block a photon include glass, metal, quartz or plastic.

A mirrored surface of the screen can consist of any material that efficiently reflects undiffused radiation. Radiation reflected by the mirrored surface can include all or a portion of the wavelengths in a radiation beam that contact the surface. For example, a screen can reflect radiation in one region of the spectrum and absorb radiation in another region. Accordingly, the mirrored surface of a screen can selectively reflect radiation in a particular region of the spectrum that is different from the range of radiation blocked by the screen material. Examples of mirrored surfaces that can efficiently reflect undiffused radiation include, for example, polished metals, metal coated glass, metal coated quartz or plastic. Examples of metals that can form a mirror when coated on glass or quartz include aluminum, silver, platinum or gold.

A mirrored surface can have any shape or orientation with respect to the direction of propagation of a radiation beam so long as a location of a radiation beam's reflection on the surface can be accurately detected and correlated with the direction of propagation for the radiation beam. Both the shape and the orientation of the mirrored surface can influence the correlation between the change in the radiation beam direction and the change in location of the reflection. For example, the distance a radiation beam reflection moves on a planar mirrored surface in response to a change in the direction of the radiation beam will depend upon the angle of the surface with respect to the direction of propagation of the radiation beam. In addition, a change in location of a reflection on a non-planar surface, such as a convex or concave surface, will have a different dependence on changes in beam direction compared to each other and compared to a planar mirrored surface when placed at similar orientations. Using well known geometric principles, one skilled in the art can select an orientation or shape for a mirrored surface that produces a desired correlation between a reflected image and the direction of a radiation beam.

A pin hole of the invention can have a variety of shapes including, for example, circular or elliptical. The shape of the pin hole can be such that efficient passage of an aligned beam is provided for a particular orientation of the mirrored surface with respect to the direction of beam propagation. For example, a pin hole can have an elliptical shape with dimensions that provide a circular area when the ellipse is rotated at a specified angle. An advantage of a screen with a mirrored surface and elliptical shaped hole is that the mirrored surface can be placed at an angle to reflect misaligned radiation to a detector while providing a circular area of passage for an aligned radiation beam. The resulting circular area of passage is advantageous because it provides a uniform radius within which an aligned radiation beam is confined.

The orientation at which a pin hole passes through a screen can be one of a variety of angles with respect to the reflective surface. For example, a screen with a planar mirrored surface can have a pin hole oriented at a substantially non-orthogonal angle with respect to the planar surface. Accordingly, the mirrored surface can be placed at a non-orthogonal angle relative to the direction of propagation of a radiation beam such that the pin hole is oriented parallel to the direction of the beam. A parallel orientation of the pin hole can be advantageous in reducing reflection or scatter of a radiation beam at the wall of the pin hole.

A screen of the invention having a mirrored surface interrupted by one or more pin holes passing through the screen can be connected to a means for changing the direction of propagation for radiation beams passing through the one or more pin holes, the direction changing means and the one or more pin hole being juxtaposed. For example, as shown in FIG. 2, one or more prism such as prism 22 or prism 23 can be juxtaposed by attachment to the back of screen 22. Radiation passing through a pin hole can be directed by a juxtaposed prism to other devices in the emission optical path.

In one embodiment, a prism juxtaposed with a pin hole and attached to a screen can be rotated at an angle $\beta$ to provide orthogonal redirection of a laser beam passing through the pin hole when the mirrored surface of the screen is rotated at an angle $\beta$ with respect to an incident radiation beam. For example, screen 22, placed as shown in FIG. 2, can be positioned at an angle $\beta$ from a plane orthogonal to the propagation direction for the radiation beam directed from lens 21. Positioning screen 22 at an angle $\beta$ allows an image of a radiation beam or flow stream to be directed away from the point of incidence at an angle $2\times\beta$. Thus, help mirror 45 can be placed at a vantage that is at an angle $2\times\beta$ from the surface of screen 22, thereby directing an image from the mirrored surface of screen 22 to camera 48. Rotation of prisms 24 and 23 at an angle $\beta$ with respect to a line intersecting the pin holes to which they are juxtaposed will direct radiation beams passing through the pin holes in opposite and orthogonal directions.

The angle $\beta$ can be any angle that reflects a radiation beam to a detector including, for example, an angle in the range of 0° to 45°. An advantage of the invention is that orienting both the radiation direction changing device and mirrored surface at an angle $\beta$ according to the geometric relationships described above, can provide efficient detection of a misaligned beam and maximal separation of 2 aligned radiation beams by redirecting the beams in orthogonal directions. Efficient detection and redirection of the radiation beams can occur at an angle β that produces a relatively wide angle of reflection such as an angle β greater than 20°, greater than 25°, greater than 30°, greater than 35° or greater than 40°. A wide angle of reflection can be used to provide for sufficient separation of optical components. Alternatively, a more compact configuration can be achieved by using a more narrow β angle including, for example less than 20°, less than 15°, less than 10°, or less than 5°.

A radiation direction changing device of the invention can be juxtaposed with a pin hole by being attached to the screen through which the pin hole passes. The radiation direction changing device can be attached by any means including, for example, a glue, adhesive, weld, solder or a fastener such as a pin, nail, or screw. Alternatively, a radiation direction changing device can be separated from a screen so as to be detached or indirectly attached by an intermediary device. As with a juxtaposed device, a radiation direction changing device that is separated from a screen can be oriented to redirect beams passing through 2 or more pin holes of a screen in orthogonal directions. Accordingly, the radiation direction changing device can be oriented at an angle β with respect to a line intersecting the pin holes as described above.

Pin holes in a screen of the invention can be separated by a distance sufficient to allow unique passage of an individual radiation beam through each hole when multiple radiation beams are directed to the screen. The distance can be determined according to the width or cross sectional diameter of a radiation beam directed to the screen such that the distance between the holes is larger than the diameter or radius of the beam cross section. Thus, pin holes can be separated by distances in the range of 0.1 to 5 mm. When radiation beams with large diameters are directed to a screen it can be advantageous to have a separation between pin holes in the screen that is in the higher end of this range or even larger including, for example, at least 1 mm, at least 2 mm, at least 4 mm or larger. Alternatively, for radiation beams having smaller diameters pin holes can be separated by at least about 0.2 mm, or at least about 0.5 mm.

A screen having a mirrored surface interrupted by one or more pin holes or an apparatus of the invention incorporating the screen can be used to determine alignment of a radiation beam. The high resolution of image formation on the mirrored surface provides for accurate determination of alignment by monitoring properties of the image produced by a sample or radiation beam including, for example, focus, shape or location. Focus of a radiation beam can be determined according to the diameter, or cross sectional shape of its reflection on the mirror. Sharpness of an image reflected by the mirror can also be used to determine focus. For example, focus of a sample in a flow chamber can be determined according to the sharpness of edges in the sample as reflected on the mirrored surface. The location of a reflection of a radiation beam relative to a pin hole on the mirrored surface can be used to determine the direction at which the beam is propagated. Because the mirrored surface can reflect both the radiation beam and sample, the alignment of the beam relative to the sample can be directly observed. Thus, the alignment of the beam with the sample and with the pin hole can be determined simultaneously at a single point of observation.

Alignment of a flow cytometer of the invention can also be determined using a forward camera 63 placed to observe a flow chamber 10 along a forward scatter path at a vantage opposite the entry point of the excitation beam. Such a placement of camera 63 can allow observation of a sample stream and excitation radiation beam to determine their alignment. Forward camera 63 can be placed to have a separate vantage from that of camera 48 as shown in FIG. 2, where the vantage of forward camera 63 is orthogonal to that of camera 48. Observation of the sample stream and excitation radiation beam from separate vantages can provide greater ease of alignment than available from a single vantage.

A dichroic beam splitter 57 that transmits excitation radiation while reflecting radiation to which the camera is sensitive can be placed to reflect an image from flow chamber 10 to forward camera 63. Dichroic beam splitter 57 can be placed beyond aperture 56 such that an image directed from lens 53 and lens 55 and filtered by filter 54 is reflected to camera 63. A lens 61 can be placed to focus an image from dichroic beam splitter 57 to camera 63. Additionally, a filter 62 can be placed in front of forward camera 63 to block residual excitation radiation. Additionally, lens 61 can be placed to focus scattered radiation to forward camera 63. A neutral density filter 62 can also be placed to attenuate the intensity of radiation reflected from dichroic beam splitter 57 that reaches forward camera 63.

The invention further provides a flow system including (a) a vacuum manifold having an internal cavity with 3 openings; (b) a sample container seal; (c) a first tube removably connected to a first of the 3 openings in the vacuum manifold, the first tube removably connected to the sample container seal, wherein the first tube passes through the sample container seal; (d) a second tube removably connected to a second of the 3 openings in the vacuum manifold; (e) a nozzle removably connected to the second tube, wherein a discharge opening of the second tube occurs in the nozzle, and (f) a third tube removably connected to a third of the 3 openings in the vacuum manifold, wherein a vacuum applied to the third tube can evacuate the first and second tubes.

A flow system of the invention can be used in a flow cytometer to deliver a sample stream to a flow chamber. A sample containing biological particles can be forced from a sample container and through a small diameter sample tube so that the particles become aligned for individual passage in a stream emerging from a discharge opening of a nozzle into a flow chamber. A stream emerging from a discharge opening of a nozzle can be directed in a vertical downward direction to cross a zone of detection in a flow chamber which intersected by a horizontal radiation beam path and observed by a detector. Particles individually entering the zone of detection can be individually identified according to one or more responses to the radiation beam including, for example, absorption of radiation, emission of fluorescence, or scatter of radiation.

Figure 6:
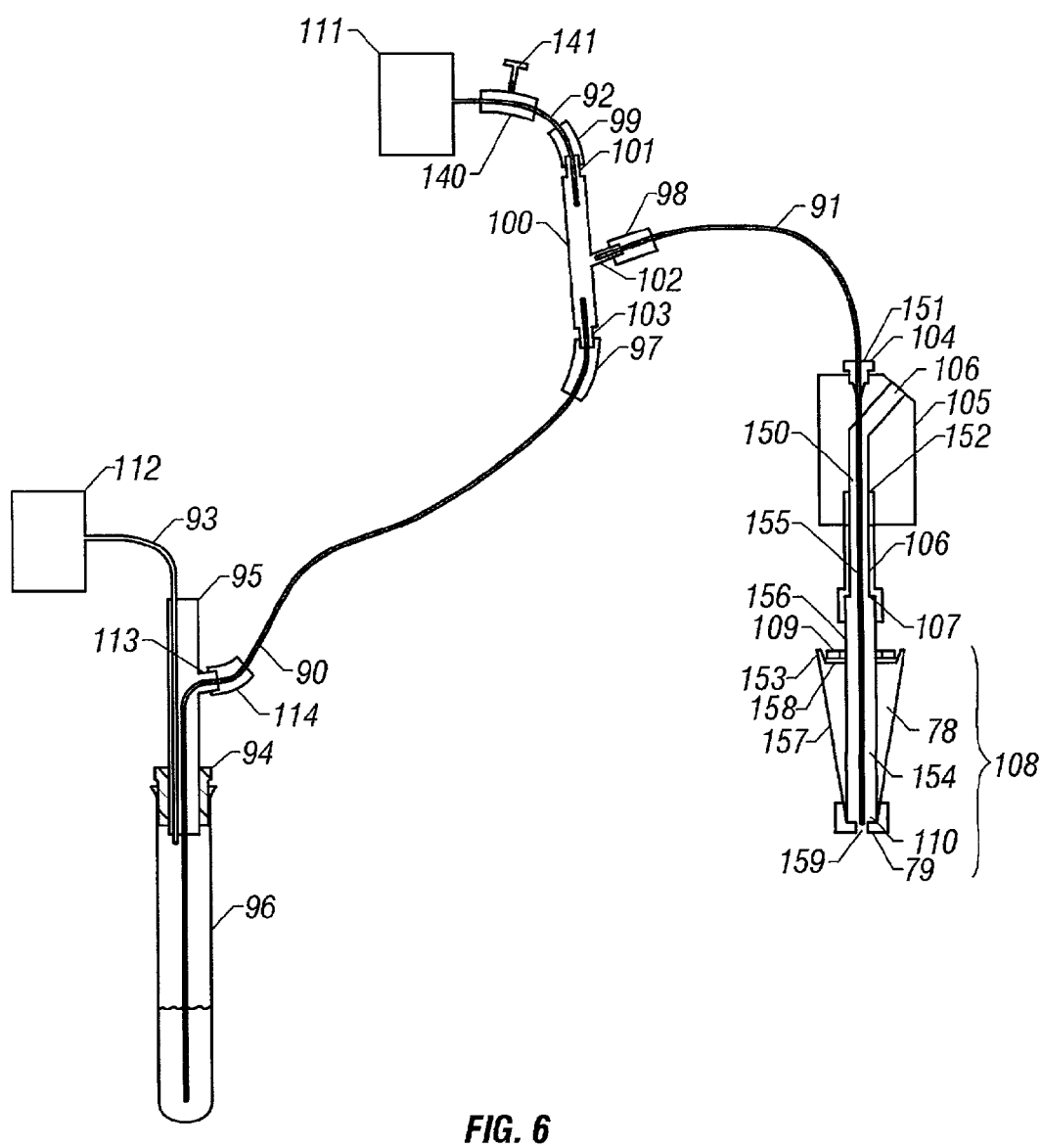
FIG. 6 shows a flow system of the invention.

A flow system of the invention can include a means for attaching a vacuum source to provide evacuation of sample tubes for decontamination between sample applications or to remove unwanted bubbles from the flow system. A vacuum source can be removably attached to an end of the flow system, for example, at the opening of tube 93 or the discharge opening of tube 91. Alternatively, and as shown in FIG. 6, a vacuum manifold 100 have an internal cavity open to three or more separate openings including, for example, opening 101, opening 102 and opening 103 can be placed at a point within the flow system. Vacuum manifold 100 can removably connect three separate tubes such that the internal spaces of all three tubes converge within the vacuum manifold. A sample tube 90, can be connected to opening 103 of vacuum manifold 100, having a second end that contacts a sample within a sample container 96. A second sample tube 91 connected to vacuum manifold 100 can have a second end that has a discharge opening in a nozzle 108. Thus, the flow system of the invention can provide transfer of a sample from a sample container 96 to a nozzle 108 using two tubes. A vacuum tube 92 can operationally connect vacuum manifold 100 to a vacuum source 111. Activation of vacuum source 111 can be used to evacuate vacuum manifold 100, sample tube 90 and sample tube 91.

A flow system of the invention can further include a sample tube support 95 capable of passing sample tube 90 and a pressure tube 93. Sample tube support 95 can be connected to sample container 96 by a sample container seal 94. Sample container seal 94 can have a hollow bore capable of passing sample tube 90 and pressure tube 93 so that the tubes and container can form a continuous system. An inner surface of sample container seal 94 can contact an outer surface of pressure manifold 95 and an outer surface of sample container seal 94 can contact an inner surface of sample container 96 to form an airtight seal when pressure is applied through pressure tube 93. Pressure can be applied through pressure tube 93 from an attached pressure source 112 thereby forcing a sample liquid sequentially through sample tube 90, vacuum manifold 100 and sample tube 91 for discharge through nozzle 108. A sample can be forced through a flow system of the invention by applying a pressure of at least 10 pounds per square inch to a sample container.

One skilled in the art will know or be able to determine an appropriate pressure to apply to the flow system to achieve a desired flow rate. The amount of pressure to be applied can be determined, for example, by routine measurements of flow rates at different pressures. A flow rate can be measured as the volume of liquid passing through a discharge opening of a sample tube during a defined time period. A flow system of the invention can be used with a flow rate of at least 0.5 ml/hour. The flow rate can be increased to a rate of at least 1 ml/hour or at least 10 ml/hour. This range of flow rates can be used to pass biological particles individually through a nozzle discharge opening in single file at a rate of at least 40,000 particles per second. Pressure can be increased or the concentration of particles can be increased to achieve a flow rate of at least 50,000 particles per second, at least 70,000 particles per second, or at least 100,000 particles per second. Alternatively, pressure or particle concentration can be decreased to achieve a flow rate of at least 30,000 particles per second, at least 20,000 particles per second, or at least 10,000 particles per second.

A flow system of the invention can further include a mixing manifold 105 having an elongated internal cavity 150 with three or more openings. A sample tube entry opening 151 can be placed to allow passage of sample tube 91 through internal cavity 150 and out of exit opening 152. Cavity 150 can have a diameter larger than the diameter of a sample tube 91 that passes through it so that a fluid entering through opening 106 can flow through elongated cavity 150 as a fluid sheath around sample tube 91. Opening 151 can be placed directly above exit opening 152 to allow sample tube 91 to pass straight through cavity 150. Opening 106 can be placed at an angle to the vertical trajectory of tube 91. Alternatively, a sheath fluid can enter a mixing manifold of the invention through an opening placed directly above an exit opening and a sample tube can enter at an angle to a vertical trajectory of a sheath fluid. Any orientation of sheath cavity and sample tube can be used so long as the sheath fluid flow is sufficiently laminar to hydrodynamically focus a sample stream into a core fluid stream. Examples of orientations for sheath and sample tubes that can be used in a mixing manifold of the invention are described in Shapiro (1995), supra.

A nozzle 108 can be removably connected to mixing manifold 105 to form a discharge opening through which liquid traveling through cavity 150 or tube 91 can exit. A nozzle 108 of the invention can have an internal cavity 154 with an entry opening 107 placed opposite a discharge opening 110. Entry opening 107 can be removably connected to mixing manifold 105 to form a continuous elongated cavity through which a sheath fluid and sample tube can pass. As shown in FIG. 6, nozzle 108 can be attached to mixing manifold 105 by an extension pipe. Removable connection of nozzle 108 to a mixing manifold or extension pipe can occur, for example, by screw thread connection.

A flow system of the invention can include a spacer placed to position discharge opening 159 of tube 91 centrally within discharge opening 110 of nozzle 108. A spacer can have a central hub portion through which sample tube 91 extends, an outer ring portion that contacts the barrier surrounding cavity 154, and a plurality of spokes connecting the central hub portion and outer ring portion. Spaces between the spokes can provide flow paths for sheath fluid flowing through cavity 154. A spacer useful in the invention is described in U.S. Pat. No. 5,819,948, which is incorporated herein by reference.

A fluid stream passing through discharge opening 110 of nozzle 108 can be induced to form droplets at a regular interval, size or distance from discharge opening 110 when oscillated within the natural frequency range of a fluid stream emerging from discharge opening 110. The point at which a fluid stream forms droplets is commonly referred to in the art as the break-off point. A nozzle of the invention can vibrate with a flat frequency spectrum which can be tuned to match the speed and diameter of a fluid jet emitted from the nozzle. Nozzle 108 can be induced to oscillate by the action of a connected oscillator 109. The frequency at which oscillator 109 oscillates can be controlled by application of an alternating voltage. Examples of oscillators useful for causing a vibration in a nozzle of the invention include a piezoelectric element or electromagnetic transducer. One skilled in the art will be able to determine appropriate oscillation frequency to achieve desired droplet interval, size or distance from discharge opening 110 using known methods as described, for example, in Shapiro, (1995), supra.

Nozzle 108 can include a shoe for removably connecting an oscillator 109. As shown in FIG. 6, a shoe can have a base 158 that is recessed or bound by one or more region of raised perimeter 153. An extended body 156 of nozzle 108 can pass through base 158 thereby forming an additional boundary for connected oscillator 109. Oscillator 109 can be shaped as a plate or disk with a perforation such that, when oscillator 109 is placed in the shoe, the perimeter of oscillator 109 fits within raised perimeter 153 and around extended body 156. Oscillator 109 when placed in the shoe of nozzle 108 will be held tightly by the above described boundaries such that, when an alternating voltage is applied to oscillator 109, its oscillations will be transferred to the discharge opening 110 of nozzle 108 causing an emerging liquid to form droplets, as described above. A nozzle of the invention can further include a nozzle described in U.S. Pat. No. 5,819,948 or U.S. Pat. No. 6,003,678, which are incorporated herein by reference.

Tubes used in the flow system of the invention including, for example, sample tube 90 and sample tube 91 can be removably connected to other components of the flow system, thereby allowing rapid and convenient replacement.

Removable connection can be achieved, for example, as shown in FIG. 6, where tube 90 is attached to vacuum manifold 100 by passing through opening 103 and being held in place by an outer sheath 97 that wraps around an outer surface of opening 103 and an outer surface of tube 90 to form a gas tight closure. A convenient outer sheath can be a short section of tubing including, for example, TYGON™ tubing. An advantage of a flow system of the invention is that replacement of tubes between sample applications provides an effective method for reducing unwanted sample carry over.

Additionally, sample tubes can be selected to accommodate particles of different sizes in the flow system. A sample tube that has a diameter of 300 micrometers or less can be used to pass a variety of biological particles including, for example, cells. To align smaller particles for individual passage through a discharge opening, a smaller diameter tube can be used in the flow system including, for example, a tube that is at least 150 micrometers in diameter, at least 100 micrometers in diameter, at least 75 micrometers in diameter, at least 50 micrometers in diameter or at least 20 micrometers in diameter or smaller.

A flow system of the invention can be controlled by a valve or other device capable of reducing or preventing passage of a liquid or gas. In one embodiment a flow cytometer of the invention can include a zero volume pinch placed to contact a flexible tube of a flow system. An example of a zero volume pinch valve attached operably attached to a flow system of the invention is shown in FIG. 6. A zero volume pinch valve operates by applying an external pressure on a flexible tube thereby reducing or preventing passage of a liquid or gas past the point of applied pressure. A zero volume pinch valve of the invention can include a body 140 through which a tube 92 passes. Body 140 can be adjustably attached to a clamping device 141 capable of alternatively compressing a tube 92 passing through the body or allowing expansion of the tube 92. An advantage of a zero volume pinch valve of the invention is that it can control the rate or volume of liquid passing through a tube without directly contacting the liquid. Thus, a zero volume pinch valve does not require decontamination or replacement between sample applications.

The invention further provides a flow cytometer capable of attaching a nozzle having a discharge opening, including (a) a means for directing a radiation beam in a horizontal path; (b) an adjustable bracket, the adjustable bracket having a means for attaching a nozzle having a discharge opening, wherein the adjustable bracket is placed to direct the discharge opening of the nozzle above the horizontal path, and (c) a means for adjusting the adjustable bracket, the adjusting means pivoting the discharge opening of the attached nozzle in an arc parallel to the horizontal path of the radiation beam. A flow cytometer of the invention can further include a separate means for adjusting the adjustable bracket, wherein the separate adjusting means moves the discharge opening in a vertical path orthogonal to the horizontal path of the radiation beam. Alternatively, a separate adjusting means can move the discharge opening in a horizontal path orthogonal to the horizontal path of the radiation beam.

An adjustable bracket 81 can be placed to direct a nozzle 108 toward a flow chamber and an excitation radiation beam passing through the flow chamber, for example, as shown in FIG. 4. Adjustable bracket 81 can be placed above a horizontal beam path by attachment to a rigid frame 160. Nozzle 108 can be attached to adjustable bracket 81 directly or through a mixing manifold 105. For example, a screw, pin, clamp or adhesive material can be used to fasten mixing manifold 105 to a surface of adjustable bracket 81 and nozzle 108 can be attached to mixing manifold 105 as described above. Movement of adjustable bracket 81 can alter the position of connected nozzle 108 relative to an excitation radiation beam to increase detection accuracy or modify detection conditions as described below. An adjustable bracket can move an attached nozzle in three mutually orthogonal directions using separate adjusting devices. An adjustable bracket can further include separate devices for adjusting pitch and yaw angles along the vertical axis.

The invention provides adjustment of an adjustable bracket to move the discharge opening of a connected nozzle in a horizontal path orthogonal to the horizontal path of the radiation beam. Such movement can be used to alter the location of a sample stream such that the excitation radiation beam and sample stream coincide for accurate detection. The adjustable bracket provides the advantage of aligning a flow system and optic system without requiring alignment of individual components of the optic system.

The invention provides adjustment of an adjustable bracket to move the discharge opening of a connected nozzle in an arc parallel to a horizontal radiation beam path. Generally, it is desirable in flow cytometry to have a vertically directed sample stream in order to minimize the cross sectional area excited by a horizontal radiation beam and to maintain accurate collection of sorted droplets. An adjustable bracket of the invention can be used to alter the angle of the discharge opening relative to the orientation of the frame upon which it is supported such that a discharged fluid stream can flow vertically when the frame is placed upon an uneven or sloped surface. Therefore, an advantage of the invention is that a flow cytometer having an adjustable bracket of the invention can be used on a surface that is not level.

The invention provides vertical adjustment of an adjustable bracket. An adjustable bracket can be moved vertically to raise or lower the discharge opening of an attached nozzle relative to a fixed horizontal radiation beam path, thereby altering the location along a discharged sample stream at which radiation is contacted. Such an alteration can allow convenient adjustment of the detection point relative to the drop breakoff point without requiring movement of a properly aligned excitation radiation beam path. Thus, a flow cytometer of the invention can readily accommodate streams with different break off points or detection at different distances from a break-off point.

A flow cytometer of the invention can include a drop camera 52 placed to observe a sample discharged from a nozzle tip. As shown in FIG. 2, drop camera 52 can be placed at a vantage capable of observing a sample stream or droplets that break off from the stream. Thus, a drop camera can be used to monitor qualities of the stream or drops including, for example, trajectory, drop size, break-off point, or drop interval. An illumination diode 171 can be included to facilitate observation of the stream or drops. Illumination diode 171 can project light of any wavelength, preferably the wavelength will be longer than that detected by emission and scatter detectors to avoid interference with sample detection. A lens 50 can be placed between the flow chamber 10 and drop camera 52 for projecting an image of the drops or drop break-off point, onto the sensitive area of camera 52. Additionally, a filter 51 can be placed in front of drop camera 52 in order to block excitation radiation while passing radiation from an illumination diode 171. In one embodiment, the illumination diode 171 can illuminate in the IR region and filter 51 can be a long pass filter with a cut on wavelength that is below the IR illumination produced by the diode and above the highest excitation wavelength contacting the sample stream. Placement of window 49 in the path from flow chamber 10 to drop camera 52 can seal the flow chamber while allowing light from the illumination diode 171 to reach drop camera 52.

A flow cytometer of the invention can be used to isolate a biological particle from a mixture by droplet sorting. As described above, a flow system of the invention can align particles in a stream and a detection system can identify individual particles. A flow system of the invention can further break the stream into droplets containing individual particles. A droplet containing a particle detected to have a desirable property can be charged and isolated from the other droplets by deflection toward a charged deflection plate. Methods of drop sorting useful in a flow cytometer of the invention are known in the art as described, for example, in Shapiro, supra.

A flow cytometer of the invention can include a deflection plate 76 capable of being electrically charged. As shown in FIG. 4, deflection plate 76 can be placed below a discharge opening of nozzle 108 and below flow chamber 10 with a charged surface facing a discharged sample past a droplet break off point. Uncharged drops can be collected in a waste container located in collection chamber 161 directly below discharge opening 110 of nozzle 108. A sample collection container can be placed in sample collection chamber 161 to capture charged drops deflected by deflection plate 76.

A deflection plate in a flow cytometer of the invention can be attached to a frame of a flow cytometer by a hinge capable of rotating a chargeable face away from a sample stream trajectory. Rotation of a deflection plate can provide improved access to the face compared to when it is facing the sample stream trajectory, thereby facilitating decontamination procedures including, for example, removal of a protective surface. The invention provides a deflection plate having its chargeable face covered by an electrically insulating tape such as PERMACELL™. An advantage of covering a deflection plate with an electrically insulating tape is that the tape can be exchanged between sample applications to minimize cross contamination of samples that can occur if the plates are not decontaminated. A tape or other covering applied to a deflection plate can be sterile to further prevent contamination of isolated samples.

Collection chamber 161 can be enclosed to provide a primary containment area. Enclosure can include portions of a rigid frame to which optical components and a flow system are attached. Additionally, a hinged door can be attached to the rigid frame to contain collection chamber 161 during sample collection and allow entry to retrieve a collected sample. A hinged door can be made of a transparent material or include a window made of a transparent material to aid in visual monitoring of sample collection. Collection chamber 161 can include an ultraviolet light source placed to optionally illuminate and sterilize the chamber following a flow sorting application. An ultraviolet light placed in a collection chamber can be connected to a switch allowing the light to be off during sample collection and on when desired samples are not present such as between flow sorting applications.

As described above, a flow cytometer of the invention provides a number of advantages for use with biological particles pertaining to decontamination between flow sorting applications. Incorporation of a flow system of the invention provides further advantages for decontamination between flow analysis or flow sorting applications. Specifically, components of a flow system of the invention that come into contact with a sample liquid can be rapidly replaced including, for example, sample tube 90 or 91, sample container 96, sample container seal 94, or nozzle 108. Replaced components can be disposed of or decontaminated separately. Thus, for diagnostic or therapeutic applications of flow cytometry or flow sorting, the flow system of the invention reduces sample carry over between application of different samples.

A rigid frame of a flow cytometer of the invention can be supported by a vibration damped platform. In one embodiment, a rigid frame can be supported by a plurality of rubber feet or feet made from another flexible material to damp transfer of vibrations to the rigid frame from a surface upon which it is placed. An advantage of the vibration damped platform is that the cytometer does not require a special optical table. Thus, a cytometer of the invention can be placed on a standard work surface found in most laboratories. The platform can further include a space for housing electronic devices for receiving detector signals, making a sort decision based on the signal received, or sending a signal to activate sorting. Such devices can include, for example, operational amplifiers, multiplier/dividers, special function transductors, comparators, logic gates or other computational hardware. Sort electronics or computational hardware for performing data acquisition or classification functions can be housed in a separate electronic route that can be placed in a separate location such as under a laboratory benchtop supporting the flow cytometer. Software and hardware for controlling sort logic and performing data acquisition or classification functions are known in the art as described, for example, in Shapiro (1995), supra.

The high degree of accuracy with which alignment and focus can be determined by an apparatus of the invention allows automation of focusing and alignment methods with an automated system. Accordingly, the invention provides an automated system for aligning a radiation beam, consisting of a camera for detecting the position of a radiation beam relative to a sample stream; a radiation beam directing device or sample stream directing device operably connected to a positioning device and a computer systems controlling movement of the positioning device by receiving a signal from the detection means and sending a processed output signal to the positioning device, wherein the output signal directs the movement of the positioning device.

An automated system for aligning a radiation beam or sample stream can include an autocentering algorithm. Autocentering algorithms are known in the art and are commonly used in microscopes to determine the location of a specimen on a microscope stage and to move the stage such that the specimen is properly aligned with an objective lens for observation. Similarly, an autocentering algorithm can be used to detect the location of a radiation beam reflection on a mirrored surface or the location at which a radiation beam crosses a sample stream and to move a device directing the radiation or sample stream such that the beam or sample stream is aligned. Alignment can also be determined from the focus of a radiation beam or sample image on a mirrored surface. Thus, an automated system can include an autofocus algorithm known in the art such as those used in microscopes and photographic cameras. Accordingly, sharpness of an edge or size or shape of a reflection from a radiation beam or sample stream can be detected and the position of a radiation beam directing device or flow system adjusted until the image is properly focused.

Thus, an automated system for aligning a radiation beam can further include a flow chamber, the flow chamber being optionally attached to a positioning device. For example, a nozzle through which a sample stream is directed can be attached to a positioning device such that movement of the nozzle alters the trajectory of the sample stream. The trajectory of the sample stream can be monitored from its reflection on a mirrored surface and the nozzle position adjusted until the reflection of the sample stream is focused or aligned according to the criteria described above. An automated system for aligning a radiation beam can further include a means for directing radiation from a radiation source to a flow chamber, the radiation directing means optionally attached to a positioning device. For example, and as described above, a lens can be used to focus a radiation beam on a sample. The position of the lens can be adjusted and the location at which the radiation beam contacts a sample stream monitored by a forward camera or camera directed to a pin hole mirror until a desired focus or alignment is achieved.

The invention further provides an apparatus including (a) a flow chamber, having two separate points capable of being contacted by separate radiation beams; (b) a first reflective surface placed to direct a first excitation radiation beam to a first of the two separate points of the flow chamber; (c) a second reflective surface placed to direct a second excitation radiation beam to a second of the two separate points of the flow chamber; (d) two or more devices for separately directing the first and second excitation radiation beams to the two separate points of the flow chamber, wherein the first excitation radiation beam passes orthogonally through a vertical plane in a forward direction, wherein the second excitation radiation beam passes through the vertical plane in a forward direction; (e) a device for directing first and second emission radiation beams from the two separate points of the flow chamber, wherein the emission radiation beams pass through the vertical plane in a reverse direction compared to the forward direction; (f) a detector module, the detector module placed to contact the first and second radiation beams; (g) a first detector connected to the detector module, wherein the first detector is placed to detect the first radiation beam; (h) a second detector connected to the detector module, the second detector being placed to detect the second radiation beam, wherein the first and second detectors are placed on the same side of the vertical plane; (i) an adjustable bracket, the adjustable bracket having a means for attaching a nozzle, wherein the adjustable bracket is placed to direct an attached nozzle toward the two separate points of the flow chamber, and (j) a means for adjusting the adjustable bracket, the adjusting means pivoting the nozzle in an arc parallel to the horizontal path of the radiation beam.

Throughout this application various publications have been referenced. The disclosures of these publications in their entireties are hereby incorporated by reference in this application in order to more fully describe the state of the art to which this invention pertains.

Although the invention has been described with reference to the examples provided above, it should be understood that various modifications can be made without departing from the spirit of the invention. Accordingly, the invention is limited only by the claims.

What is claimed is:

1. A flow cytometer, comprising:
   (a) a flow chamber;
   (b) a first reflective surface placed to direct an excitation radiation beam to said flow chamber;
   (c) one or more devices for directing an excitation radiation beam to said first reflective surface, wherein said excitation radiation beam passes orthogonally through a vertical plane in a forward direction;
   (d) a device for directing an emission radiation beam positioned adjacent to said flow chamber, wherein said emission radiation beam passes through said vertical plane in a reverse direction compared to said forward direction, and
   (e) a sample tube having a discharge opening directed to said flow chamber and a removably connected oscillator, said oscillator capable of vibrating at a frequency that produces droplets from a stream emerging from said sample tube.

2. The flow cytometer of claim 1, further comprising:
   (e) a second reflective surface placed to direct an excitation radiation beam to said first reflective surface, wherein said second reflective surface is placed at a different elevation compared to said first reflective surface.

3. The flow cytometer of claim 1, further comprising:
   (e) a radiation source placed to direct a radiation beam to said first reflective surface.

4. The flow cytometer of claim 3, wherein said radiation source is a laser.

5. The flow cytometer of claim 1, wherein said discharge opening has a diameter of 300 micrometers or less.

6. The flow cytometer of claim 1, further comprising a pressure source providing pressure to said sample tube.

7. The flow cytometer of claim 6, wherein said pressure source provides at least 10 pounds per square inch to said sample tube.

8. The flow cytometer of claim 1, further comprising a second reflective surface placed to direct a second excitation radiation beam to said flow chamber.

9. The flow cytometer of claim 8, further comprising a second device for directing said second excitation radiation beam to said second reflective surface, wherein said second excitation radiation beam passes through said vertical plane in a forward direction.

10. The flow cytometer of claim 8, further comprising separate lenses placed to separately focus said first and second excitation radiation beams on said flow chamber.

11. The flow cytometer of claim 8, further comprising a third reflective surface placed to direct a third excitation radiation beam to said flow chamber.

12. The flow cytometer of claim 11, further comprising a third device for directing said third excitation radiation beam to said third reflective surface, wherein said third excitation radiation beam passes through said vertical plane in a forward direction.

13. The flow cytometer of claim 11, further comprising separate lenses placed to separately focus said first second and third excitation radiation beams on said flow chamber.

14. The flow cytometer of claim 1, further comprising an alignment pin hole placed to pass an excitation radiation beam from said first reflective surface to said flow chamber.

15. The flow cytometer of claim 1, wherein said flow chamber, said first reflective surface, said device for directing an excitation radiation beam, and said device for directing an emission radiation beam occur within an area having dimensions of 15 inches by 9 inches or smaller.

16. The flow cytometer of claim 1, further comprising a camera placed to observe a radiation beam contacting said flow chamber.

17. The flow cytometer of claim 16, wherein said camera is placed to observe said flow chamber at a vantage opposite an entry point of said radiation beam.

18. A flow cytometer comprising:
   (a) a flow chamber, having two separate points capable of being contacted by separate radiation beams;

(b) a first reflective surface placed to direct a first excitation radiation beam to a first of said two separate points of said flow chamber;
(c) a second reflective surface placed to direct a second excitation radiation beam to a second of said two separate points of said flow chamber;
(d) two or more devices for separately directing said first and second excitation radiation beams to said two separate points of said flow chamber, wherein said first excitation radiation beam passes orthogonally through a vertical plane in a forward direction, wherein said second excitation radiation beam passes through said vertical plane in a forward direction;
(e) a device for directing first and second emission radiation beams from said two separate points of said flow chamber, wherein said emission radiation beams pass through said vertical plane in a reverse direction compared to said forward direction;
(f) a detector module, said detector module placed to contact said first and second radiation beams;
(g) a first detector connected to said detector module, wherein said first detector is placed to detect said first radiation beam;
(h) a second detector connected to said detector module, said second detector being placed to detect said second radiation beam, wherein said first and second detectors are placed on the same side of said vertical plane;
(i) an adjustable bracket, said adjustable bracket having a means for attaching a nozzle, wherein said adjustable bracket is placed to direct an attached nozzle toward said two separate points of said flow chamber, and
(j) a means for adjusting said adjustable bracket, said adjusting means pivoting said nozzle in an arc parallel to said horizontal path of said radiation beam.

19. A flow cytometer, comprising:
(a) a flow chamber;
(b) first and second reflective surfaces placed to direct first and second excitation radiation beams to said flow chamber;
(c) two or more devices for directing first and second excitation radiation beams to said first and second reflective surfaces, wherein said excitation radiation beams pass orthogonally through a vertical plane in a forward direction, and
(d) a device for directing emission radiation beams from said flow chamber, wherein said emission radiation beams passes through said vertical plane in a reverse direction compared to said forward direction.

20. The flow cytometer of claim 19, further comprising:
(e) a third reflective surface placed to direct an excitation radiation beam to said first or second reflective surfaces, wherein said third reflective surface is placed at a different elevation compared to said first or second reflective surfaces.

21. The flow cytometer of claim 19, further comprising:
(e) one or more radiation sources placed to direct a radiation beam to said first or second reflective surface.

22. The flow cytometer of claim 21, wherein said one or more radiation sources is a laser.

23. The flow cytometer of claim 19, further comprising a sample tube having a discharge opening directed to said flow chamber.

24. The flow cytometer of claim 23, wherein said discharge opening has a diameter of 300 micrometers or less.

25. The flow cytometer of claim 24, further comprising a pressure source providing pressure to said sample tube.

26. The flow cytometer of claim 25, wherein said pressure source provides at least 10 pounds per square inch to said sample tube.

27. The flow cytometer of claim 23, further comprising an oscillator removably connected to said sample tube, said oscillator capable of vibrating at a frequency that produces droplets from a stream emerging from said sample tube.

28. The flow cytometer of claim 19, further comprising separate lenses placed to separately focus said first and second excitation radiation beams on said flow chamber.

29. The flow cytometer of claim 19, further comprising a third reflective surface placed to direct a third excitation radiation beam to said flow chamber.

30. The flow cytometer of claim 29, further comprising a third device for directing said third excitation radiation beam to said third reflective surface, wherein said third excitation radiation beam passes through said vertical plane in a forward direction.

31. The flow cytometer of claim 30, further comprising separate lenses placed to separately focus said first second and third excitation radiation beams on said flow chamber.

32. The flow cytometer of claim 19, further comprising an alignment pin hole placed to pass an excitation radiation beam from said first reflective surface to said flow chamber.

33. The flow cytometer of claim 19, wherein said flow chamber, said first and second reflective surfaces, said two or more devices for directing an excitation radiation beam, and said device for directing emission radiation beams occur within an area having dimensions of 15 inches by 9 inches or smaller.

34. The flow cytometer of claim 19, further comprising a camera placed to observe a radiation beam contacting said flow chamber.

35. The flow cytometer of claim 34, wherein said camera is placed to observe said flow chamber at a vantage opposite an entry point of said radiation beam.

* * * * *